United States Patent
Kim et al.

(10) Patent No.: US 10,267,794 B2
(45) Date of Patent: Apr. 23, 2019

(54) LSPR-BASED HIGH SENSITIVITY APTAMER SENSOR USING INTERCALATION AGENT

(71) Applicant: GWANGJU INSTITUTE OF SCIENCE AND TECHNOLOGY, Gwangju (KR)

(72) Inventors: Min-Gon Kim, Gwangju (KR); Jin-Ho Park, Gwangju (KR); Ju Young Byun, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 22 days.

(21) Appl. No.: 15/418,100

(22) Filed: Jan. 27, 2017

(65) Prior Publication Data

US 2017/0219572 A1    Aug. 3, 2017

(30) Foreign Application Priority Data

Jan. 28, 2016    (KR) ........................ 10-2016-0010374

(51) Int. Cl.
| | | |
|---|---|---|
| *C12N 15/115* | (2010.01) | |
| *G01N 33/543* | (2006.01) | |
| *G01N 33/58* | (2006.01) | |
| *G01N 33/53* | (2006.01) | |
| *G01N 33/542* | (2006.01) | |

(52) U.S. Cl.
CPC ... *G01N 33/54386* (2013.01); *G01N 33/5308* (2013.01); *G01N 33/542* (2013.01); *G01N 33/587* (2013.01); *C12N 15/115* (2013.01); *C12N 2310/16* (2013.01); *C12N 2320/10* (2013.01)

(58) Field of Classification Search
CPC .............. C12N 15/115; C12N 2310/16; C12N 2320/10; G01N 21/554
USPC ............... 428/402; 435/6.1, 6.12, 91.1, 6.11, 435/91.31; 436/174; 536/23.1, 24.3, 536/24.5; 424/9.1
See application file for complete search history.

(56) References Cited

U.S. PATENT DOCUMENTS

2013/0143331 A1*    6/2013    Ginger ................. C12Q 1/6834
                                                    436/174

* cited by examiner

*Primary Examiner* — Jane J Zara
(74) *Attorney, Agent, or Firm* — Hauptman Ham, LLP

(57) ABSTRACT

Disclosed herein is an aptamer sensor including a substrate having metal nanoparticles formed thereon, an aptamer attached to surfaces of the metal nanoparticles to form a structure by selectively reacting with a target material to be detected, and an intercalating agent inserted between the aptamer and the target material in reaction of the aptamer with the target material to increase shift of an absorption spectrum due to local surface plasmon resonance sensor through aggregation toward the metal nanoparticles.

5 Claims, 3 Drawing Sheets

Specification includes a Sequence Listing.

SEQUENCE LISTING

<160> NUMBER OF SEQ ID NOS: 2

<210> SEQ ID NO 1
<211> LENGTH: 44
<212> TYPE: DNA
<213> ORGANISM: Artificial
<220> FEATURE:
<223> OTHER INFORMATION: an OTA aptamer

<400> SEQUENCE: 1
tttttgggtg gcgtaaaggg ggggcgtaaa gggagcatcg gaca                44

<210> SEQ ID NO 2
<211> LENGTH: 55
<212> TYPE: DNA
<213> ORGANISM: Artificial
<220> FEATURE:
<223> OTHER INFORMATION: an AFB1 aptamer

<400> SEQUENCE: 2
tttttgttgg gcacgtgttg tctctctgtg tctcgtgccc ttcgctaggc ccaca        55

LSPR-BASED HIGH SENSITIVITY APTAMER SENSOR USING INTERCALATION AGENT

CROSS-REFERENCE TO RELATED APPLICATIONS

This application claims the priority of Korean Patent Application No. 10-2016-0010374 filed on Jan. 28, 2016, in the Korean Intellectual Property Office, the disclosure of which is hereby incorporated by reference in its entirety.

BACKGROUND

1. Technical Field

The present disclosure relates to an aptamer biosensor, and more particularly, to an aptamer sensor with improved sensitivity using a localized surface plasmon resonance (LSPR).

2. Description of the Related Art

The technology for rapidly measuring biomolecules has been recognized as an indispensable technology along with basic research on development of biosensors in medical field. Now that the relationship between the genome and the disease has become clearer by analysis of the human genome, a simple and easy-to-understand genetic diagnosis is required in the medical field, and development of relevant technology is ongoing. It is important to analyze interaction of biomolecules, but observing nanoscale biomolecules is not easy. Therefore, in recent years, researches on optical biosensors that combine biomolecules with plasmonic nanomaterials such as metal nanoparticles to observe phenomena occurring in a nano-sized space are increasingly being conducted. This is because the development of nanotechnology has made it possible to control plasmonic nanomaterials such as metal nanoparticles. Plasmonic nanomaterials are expected not only to be used as simple optical materials but also as tools for biosensor analysis.

In contrast with the case of bulk metal, when light having various wavelengths is emitted onto a material existing on a local surface such as metal nanoparticles, polarization occurs on the surface of metal nanoparticles and exhibits a unique characteristic of increasing the intensity of the electric field. Electrons formed by polarization form a group (plasmon) and locally vibrate on the surface of the metal nanoparticles. This phenomenon is called localized surface plasmon resonance (LSPR). This phenomenon has been theoretically calculated and predicted by Mie and others for a long time. Recently, as nanofabrication technology has been developed, useful researches on combination with various sensors have been published.

Similar to surface plasmon resonance (SPR), LSPR optical properties are sensitive to changes in dielectric constant, namely, refractive index, that occur near nanoparticles, allowing analysis of biomolecular interactions with relatively high sensitivity and ease. Therefore, by immobilizing various ligands on a single biochip based on LSPR optical properties as a detection principle, simultaneous analysis of multiple samples can be performed, compared to conventional biochips. Therefore, on-site monitoring required for unlabeled biochips is also possible.

The SPR phenomenon occurs in an electron-rich metal film. On the other hand, the LSPR phenomenon occurs on the surface of a nanometer-sized metal particle with a relatively limited amount of electrons, and accordingly vibration of electrons in the metal is weak, the size of the electric field caused by vibration of electrons is small. The small electromagnetic field reduces the range in which a material can be sensed, resulting in a reduced sensitivity to detect the target material. In particular, in measuring small molecular materials with low molecular weights, the limit of sensitivity is clear due to the small influence of the electromagnetic field. Therefore, there is a need for a technique for improving the sensitivity in measuring low molecular materials.

It should be understood that the foregoing description of the background art is merely for the purpose of promoting an understanding of the background of the present disclosure, and is not to be construed as admitting that the present disclosure corresponds to the prior art known to those skilled in the art.

SUMMARY

It is an object of the present disclosure to provide an aptamer sensor having sensitivity enhanced by increasing the amount of change of an absorption spectrum according to LSPR of metal nanoparticles that is changed by binding event between aptamer and target material on metal nanoparticle surface Objects of the present disclosure are not limited to the above-described objects and other objects and advantages can be appreciated by those skilled in the art from the following descriptions. Further, it will be easily appreciated that the objects and advantages of the present disclosure can be practiced by means recited in the appended claims and a combination thereof.

In accordance with one aspect of the present disclosure, an aptamer sensor includes a substrate having metal nanoparticles formed thereon, an aptamer attached to surfaces of the metal nanoparticles to form a complex structure by selectively reacting with a target material to be detected, and an intercalating agent inserted between the aptamer and the target material in reaction of the aptamer with the target material to increase shift of an absorption spectrum due to increase of local refractive index and molecular density through aggregation toward the metal nanoparticles surface.

The metal nanoparticles may be gold, platinum or silver.

The intercalating agent may be berberine.

A complex formed by the target material and the aptamer may be a G-quadruplex structure.

The target material may be either ochratoxin A (OTA) or aflatoxin $B_1$ ($AFB_1$).

A detection range of the target material may be from 1 pM to 10 µM.

With an aptamer sensor according to embodiments of the present disclosure, the sensing range of the target material may be increased, and thus the sensitivity and the detection range may be greatly increased. In particular, when berberine is used as the intercalating agent, the exiting detection range of 1 nM to 1 µM is increased to 1 pM to 10 µM, and sensitivity is increased about 1000 times.

DETAILED DESCRIPTION

Figure 1:
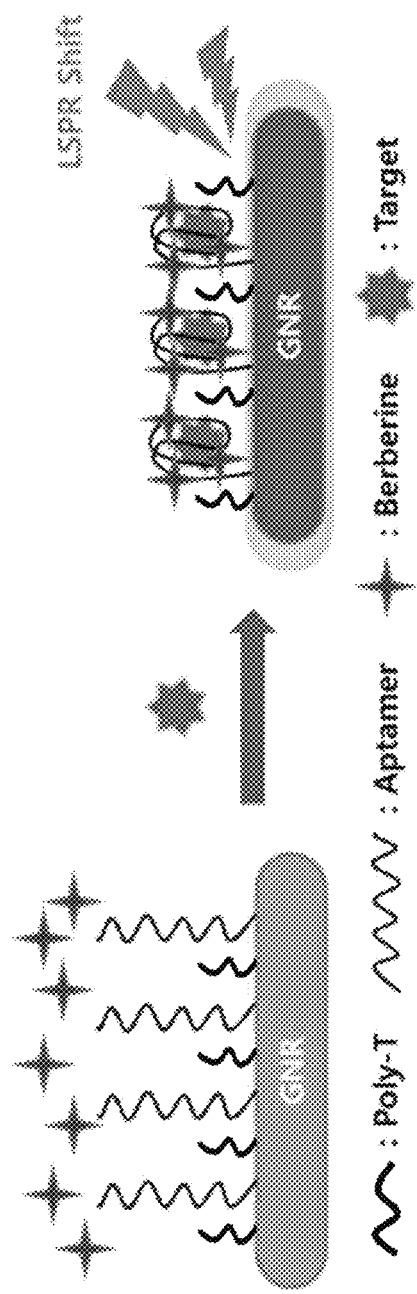
FIG. 1 is a schematic diagram illustrating an aptamer sensor according to an embodiment of the present disclosure.

It is an object of the present disclosure to provide an aptamer sensor having sensitivity enhanced by increasing the amount of change of an absorption spectrum according to LSPR of metal nanoparticles that is changed by binding event between aptamer and target material on metal nanoparticle surface.

Objects of the present disclosure are not limited to the above-described objects and other objects and advantages can be appreciated by those skilled in the art from the following descriptions. Further, it will be easily appreciated that the objects and advantages of the present disclosure can be practiced by means recited in the appended claims and a combination thereof.

In accordance with one aspect of the present disclosure, an aptamer sensor includes a substrate having metal nanoparticles formed thereon, an aptamer attached to surfaces of the metal nanoparticles to form a complex structure by selectively reacting with a target material to be detected, and an intercalating agent inserted between the aptamer and the target material in reaction of the aptamer with the target material to increase shift of an absorption spectrum due to increase of local refractive index and molecular density through aggregation toward the metal nanoparticles.

The metal nanoparticles may be gold, platinum or silver.
The intercalating agent may be berberine.
A complex formed by the target material and the aptamer may be a G-quadruplex structure.

The target material may be either ochratoxin A (OTA) or aflatoxin $B_1$ ($AFB_1$).

A detection range of the target material may be from 1 pM to 10 μM.

With an aptamer sensor according to embodiments of the present disclosure, the sensing range of the target material may be increased, and thus the sensitivity and the detection range may be greatly increased. In particular, when berberine is used as the intercalating agent, the exiting detection range of 1 nM to 1 μM is increased to 1 pM to 10 μM, and sensitivity is increased about 1000 times.

The above objects, features and advantages will become apparent from the detailed description with reference to the accompanying drawings. Embodiments are described in sufficient detail to enable those skilled in the art in the art to easily practice the technical idea of the present disclosure. Detailed descriptions of well known functions or configurations may be omitted in order not to unnecessarily obscure the gist of the present disclosure. Hereinafter, embodiments of the present disclosure will be described in detail with reference to the accompanying drawings. Throughout the drawings, like reference numerals refer to like elements.

The terminology used herein is for the purpose of describing specific embodiments only and is not intended to limit the disclosure. The singular forms used herein include plural forms as well, provided that the phrases do not expressly have the opposite meaning. As used herein, the term "include" specifies a particular feature, region, integer, step, operation, element and/or component, and does not exclude the presence or addition of one or more other particular features, regions, integers, steps, operations, elements, components, and/or groups.

Unless otherwise defined, all terms including technical and scientific terms used herein have the same meaning as commonly understood by one of ordinary skill in the art to which this disclosure belongs. Terms defined in the generic dictionary are further construed to have meanings consistent with the relevant technical literature and the present disclosure, and are not to be construed as ideal or very formal meanings unless defined otherwise.

Hereinafter, an aptamer sensor according to a preferred embodiment of the present disclosure will be described with reference to the accompanying drawings.

While surface plasmon resonance occurs in electron-rich metal films, local surface plasmon resonance occurs in nano-sized metal, which has a relatively limited amount of electrons. Accordingly, vibration of electrons in metal is weak and the size of an electromagnetic field generated by vibration of electrons is small. The small electromagnetic field results in a small detection range for detecting a target molecule, lowering sensitivity for detecting the target material. In particular, in measuring materials with small molecular weights, the influence of the electromagnetic field is small, which limits the sensitivity.

The inventor of the present disclosure has repeatedly conducted experiments to improve such sensitivity, and found that, when the complex of the aptamer formed on the surface of metal nanoparticles and the G-quadruplex structure formed by a target material is more closely aggregated toward the metal nanoparticles, the amount of shift of the absorption spectrum due to the LSPR of the metal nanoparticles is increased and thus the sensitivity of the aptamer sensor is improved. Therefore, in order to increase change of the refractive index of the surface of the metal nanoparticles when forming a complex of G-quadruplex structure by combining the aptamer material with the target material, based on this phenomenon, an intercalating agent is introduced such that a separate molecule can be additionally bound to the complex.

FIG. 1 is a schematic diagram illustrating an aptamer sensor according to an embodiment of the present disclosure. As shown in FIG. 1, the aptamer sensor according to an exemplary embodiment of the present disclosure may include a substrate, an aptamer, and an intercalating agent. Basically, metal nanoparticles are formed on a substrate. These metal nanoparticles may be metal particles capable of causing local surface plasma resonance, such as gold, silver, or platinum particles. In this embodiment, the gold nanoparticles are formed into a small rod (gold nanorod (GNR)) and introduced into a glass substrate. An aptamer capable of forming a structure by selectively reacting with a target to be detected is fixed on the surface of the gold nanorod. The aptamer corresponds to a single-stranded nucleic acid (DNA, RNA, or modified nucleic acid), which has a stable tertiary structure and can be bound to the target material with high affinity and specificity. A poly-T3 strand may be positioned between aptamers to form a certain space. These Poly-T3 strands serve to maintain a certain space when a complex is formed by the aptamers and the target material. The aptamers employed in this embodiment are an OTA aptamer (SEQ.ID.NO. 1: 5'-SH-TTTTTGGGTGGCG-TAAAGGGGGGGCGTAAAGGGAGCATCGGACA) and $AFB_1$ aptamer (SEQ.ID.NO. 2:5'-SH-TTTTTGT-TGGGCACGTGTTGTCTCTCTGTGTCTCGTGCCCT-TCGCTAGGCCCACA), but various other aptamers may also be used depending on the target material to be detected. In addition, an intercalating agent was used to aggregate more molecules into a complex when the aptamers and the target material were combined to form the complex. Preferably, the intercalating agent is berberine. The intercalating agent is attached to G-quadruplex structure when the aptamer immobilized on the surface of the gold nanorod forms G-quadruplex structure by the target material. Thereby, the ambient electromagnetic field is influenced and the width of change of the absorbance wavelength becomes large.

The present disclosure will be described in more detail with reference to experimental examples.

1. Synthesis of GNR

GNRs usable in the present disclosure were synthesized by a seed growth technique. Briefly, 0.125 mL of 0.01 M $HAuCl_4$ and 0.3 mL of 0.01 M $NaBH_4$ were mixed in a 0.1 M CTAB (cetyltrimethylammonium bromide) solution and maintained at 30° C. for 2 hours to prepare a seed solution. Meanwhile, a growth solution was prepared by mixing 33.04 ml of 0.1 M CTAB, 1.4 ml of 0.01 M $HAuCl_4$, 0.21 ml of 0.01 M $AgNO_3$ and 0.21 ml of 0.1 M ascorbic acid. 0.14 ml of the seed solution was added to the growth solution, followed by reaction at 30° C. for 3 hours. The UV/vis absorption spectrum of the GNR solution was obtained through a 96-well plate reader (Infinite M200pro, TECAN Group, Ltd., Switzerland). The size and aspect ratio were measured using a high-resolution transmission electron microscope (HR-TEM, JEM-2100, JEOL Ltd., Japan). The gold nanorods were 35.85±3.27 nm in length and 11.17±1.03 nm in width, indicating an average aspect ratio of 3.21 and even distribution.

2. Fabrication of GNR Substrate

The following method was used to fabricate a substrate with attached GNRs used in the present disclosure. A glass slide (10 mm×25 mm×0.7 mm) was washed with a piranha solution (H2SO4:H2O2=3:1) at 65° C. for 30 minutes. To form an amine surface, the glass slide was washed with DI water and ethanol and immersed in 2% APTMS ((3-aminopropyl)trimethoxysilane) solution at a room temperature for 1 hour. The amine-formed glass slide was treated with 1 M succinic anhydride in DMF (N,N-dimethylformamide) at 37° C. for 8 hours and washed with DI water. The slide treated with succinic anhydride was subjected to an amide bond formation reaction by treatment with 50 mM of EDC (N-Ethyl-N'-(3-dimethylaminopropyl)carbodiimide) and 25 mM of NHS (N-Hydroxysuccinimide) for 10 minutes, and immersed in 0.1 M cyteamine hydrochloride solution in DI water. Finally, the thiol-treated glass slide was exposed to a GNR-dispersed solution for 20 hours, and then centrifuged three times at a rate of 10,000 rpm for 15 minutes to remove CTAB of theGNRs.

3. Aptamer Binding Process

Two types of aptamers, reactive with OTA (ochratoxin A) and $AFB_1$ (aflatoxin B 1), were mixed with the same concentration of PolyT3 as a volume ratio of 1:1 or 1:2. The initial concentration of each oligonucleotide was 10 µM, and the volume of the final oligonucleotide mixture was maintained at 20 µL. The oligonucleotide mixture is reacted with 5 mM TCEP (tris (2-carboxyethyl) phosphine hydrochloride) to cleave the disulfide bond of the thiol group bound at the 5' end of the oligonucleotide. The activated thiol group of the oligonucleotide is treated with a 0.1 M glycine buffer (pH 3.0) solution for 1 hour and fixed on the surface of the GNR substrate. After washing with DI water (DW), OTA, $AFB_1$, and berberine were treated with 150 µl of a binding buffer solution (20 mM tris-HCl, 100 mM NaCl, 10 mM KCl, 10 mM MgCl2, pH 7.2) on the surface of gold nanorod substrate having a fixed aptamer at 25° C. for 30 minutes and incubated, such that the target material could bind to the aptamer. The same method was used for berberine-free treatment.

4. Detection of Local Surface Plasmon Resonance (LSPR) Signal

The GNR substrate treated with aptamer was fixed to a transparent 96-well plate. 150 µl of the binding buffer solution containing target molecules and 5 µM berberine were applied onto the fixed substrate. After 30 minutes of reaction at 25° C., the absorption spectrum was measured in the wavelength range from 650 nm to 900 nm.

First, the absorption spectrum was measured using the method as described above. In the measurement, 6 intercalating agents of berberine (BB), thioflavin T (TFT), crystal violet (CV), thiazole orange (TO), malachite green (MG) and Zn-PPix were used to confirm signal enhancement by binding affinity to the G-quadplex structure. The intercalating agents were applied to the aptamer-immobilized GNR substrate along with the target material and the binding buffer solution, and reacted for 30 minutes, and the red shift of the absorption spectrum according to additional LSPR was measured. The molecular structures of the intercalating agents used in this experimental example are as follows (See Table 1).

TABLE 1

Thiazole Orange (TO)

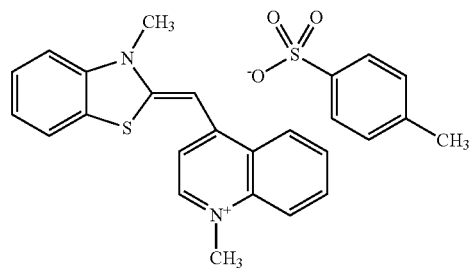

Malachite Green (MG)

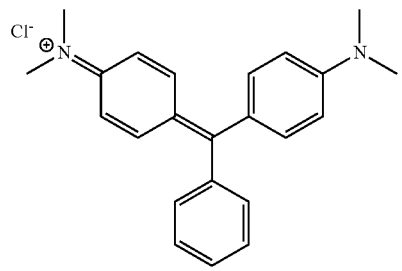

Crystal Violet (CV)

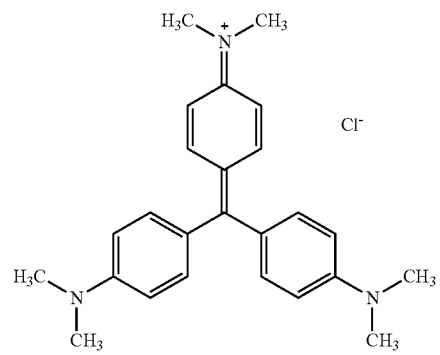

TABLE 1-continued

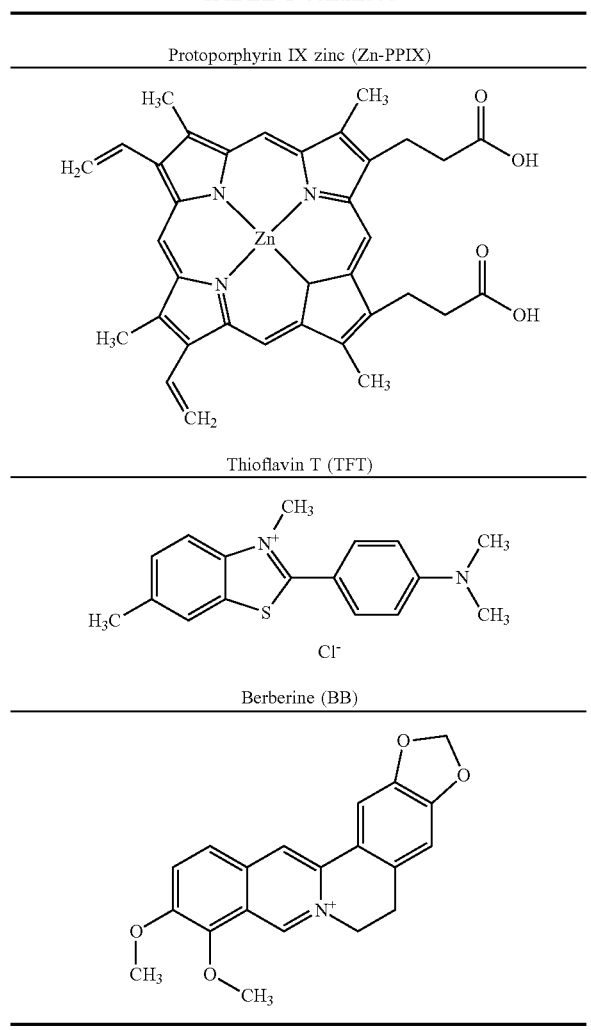

Figure 2:
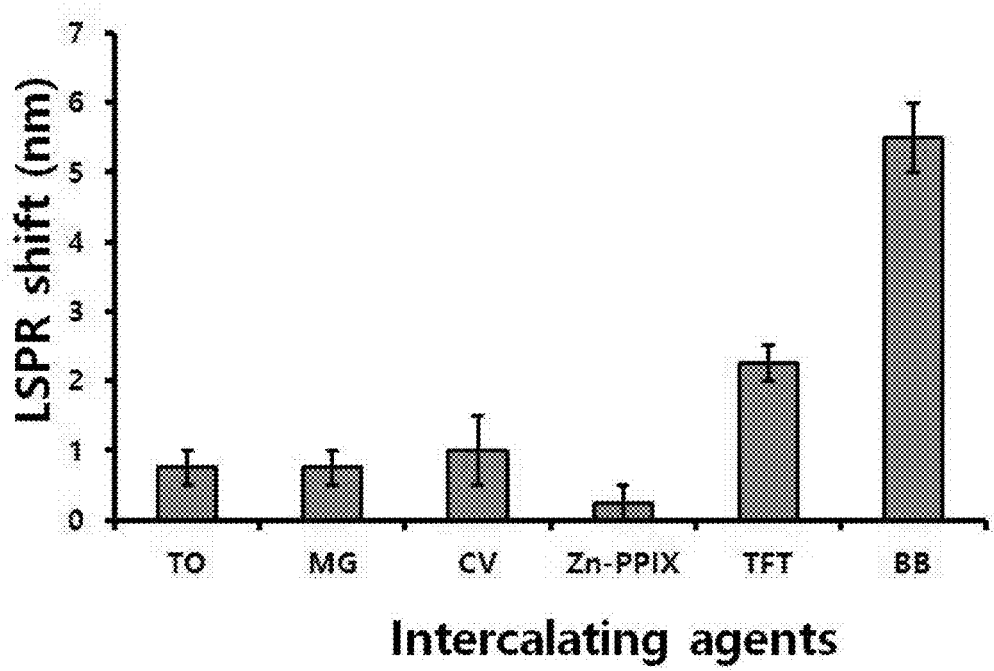
FIG. 2 is a graph depicting the amount of red shift of the LSPR absorption spectrum of the aptamer sensor according to kinds of intercalating agents.

FIG. 2 is a graph depicting the amount of red shift of the LSPR absorption spectrum of the aptamer sensor according to kinds of intercalating agents. As shown in FIG. 2, it was confirmed that LSPR shift was caused by each intercalating agent. It can be seen from the graph that berberine exhibits LSPR shift of about 5.5 nm, the largest red shift of the absorption spectrum among the intercalating agents. It can also be seen from the graph that berberine is further aggregated with the complex of G-quadruplex structure formed by binding of the aptamer and the target material and has the best sensitivity enhancement.

Figure 3:
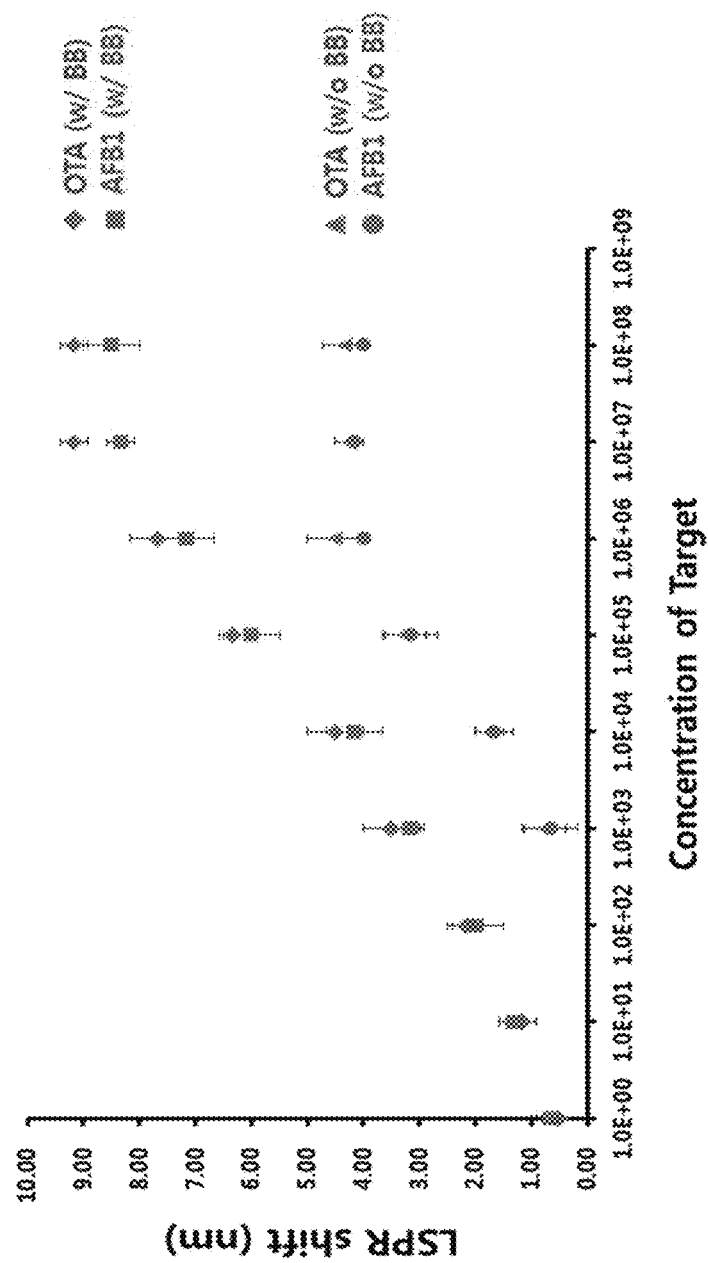
FIG. 3 is a graph depicting the amount of red shift of the LSPR absorption spectrum of the aptamer sensor depending on presence and absence of berberine according to an embodiment of the present disclosure.

LSPR shifts of an aptamer sensor in cases of presence and absence of berberine as an intercalating agent were compared by changing concentrations of OTA and $AFB_1$ used as target materials. FIG. 3 is a graph depicting the amount of red shift of the LSPR absorption spectrum of the aptamer sensor depending on presence and absence of berberine according to an embodiment of the present disclosure. As shown in FIG. 3, it was confirmed that, when berberine was present, the minimum detectable concentration was 0.001 nM, and the entire detection range was extended to a concentration range of 0.001 nM to 10 μM.

As described above, with the aptamer sensor according to the present disclosure, the amount of red shift of the absorption spectrum caused by LSPR of metal nanoparticles is increased by introducing an intercalating agent. Accordingly, the aptamer sensor is capable of detecting a very small amount of a target material.

While exemplary embodiments of the present disclosure have been described with reference to the accompanying drawings, those skilled in the art will appreciate that the disclosure may be implemented in other specific forms without changing the spirit and essential features of the disclosure.

It is therefore to be understood that the embodiments described above are illustrative in all aspects and not restrictive. The scope of protection sought by the present disclosure should be determined by the appended claims and their equivalents, and all changes coming within the meaning and equivalency range of the appended claims are intended to be embraced therein.

What is claimed is:

1. An aptamer sensor comprising:
a substrate having metal nanoparticles formed thereon;
an aptamer attached to surfaces of the metal nanoparticles to form a structure by selectively reacting with a target material to be detected; and
an intercalating agent inserted between the aptamer and the target material in reaction of the aptamer with the target material to increase the shift of an absorption spectrum due to local surface plasmon resonance phenomenon through aggregation toward the metal nanoparticles, wherein a complex formed by the target material and the aptamer is a G-quadruplex structure, and
wherein the intercalating agent is at least one selected from the group consisting of berberine (BB), thioflavin T (TFT), crystal violet (CV), thiazole orange (TO), malachite green (MG) and Zn-PPix.

2. The aptamer sensor according to claim 1, wherein the metal nanoparticles are gold, platinum or silver.

3. The aptamer sensor according to claim 1, wherein the intercalating agent is berberine.

4. The aptamer sensor according to claim 1, wherein the target material is either ochratoxin A (OTA) or aflatoxin $B_1$ (AFB$_1$).

5. The aptamer sensor according to claim 1, wherein a detection range of the target material is from 1 pM to 10 μM.

* * * * *